(12) United States Patent
Ahmad (10) Patent No.: US 10,137,275 B2
(45) Date of Patent: Nov. 27, 2018

(54) OXYGEN CONCENTRATOR FOR HIGH PRESSURE OXYGEN DELIVERY WITH OXYGEN CIRCULATION LOOP AND IMPROVED PORTABILITY

(71) Applicant: BREATHE TECHNOLOGIES, INC., Irvine, CA (US)

(72) Inventor: Samir S. Ahmad, San Diego, CA (US)

(73) Assignee: BreatheTechnologies, Inc., Irvine, CA (US)

( * ) Notice: Subject to any disclaimer, the term of this patent is extended or adjusted under 35 U.S.C. 154(b) by 956 days.

(21) Appl. No.: 14/598,637

(22) Filed: Jan. 16, 2015

(65) Prior Publication Data

US 2015/0196727 A1  Jul. 16, 2015

Related U.S. Application Data

(60) Provisional application No. 61/928,110, filed on Jan. 16, 2014.

(51) Int. Cl.
| | |
|---|---|
| *A61M 16/10* | (2006.01) |
| *A61M 16/06* | (2006.01) |
| *B01D 53/00* | (2006.01) |
| *B01D 53/053* | (2006.01) |

(52) U.S. Cl.
CPC ...... *A61M 16/101* (2014.02); *A61M 16/0677* (2014.02); *B01D 53/053* (2013.01); *A61M 16/107* (2014.02); *A61M 2202/0208* (2013.01); *A61M 2205/18* (2013.01); *A61M 2205/52* (2013.01); *A61M 2205/82* (2013.01); *B01D 2253/108* (2013.01); *B01D 2256/12* (2013.01); *B01D 2257/102* (2013.01); *B01D 2258/06* (2013.01); *B01D 2259/402* (2013.01); *B01D 2259/40003* (2013.01); *B01D 2259/4533* (2013.01); *B01D 2259/4541* (2013.01)

(58) Field of Classification Search
None
See application file for complete search history.

(56) References Cited

U.S. PATENT DOCUMENTS

| | | | |
|---|---|---|---|
| 8,361,204 B1 | 1/2013 | Bassine | |
| 8,568,519 B2 | 10/2013 | Taylor et al. | |
| 2009/0107500 A1* | 4/2009 | Edwards | A61M 16/10 128/204.23 |

(Continued)

OTHER PUBLICATIONS

ISR and Written Opinion for PCT/US2015/011826. dated May 4, 2015.

*Primary Examiner* — Rachel T Sippel
(74) *Attorney, Agent, or Firm* — Stetina Brunda Garred and Brucker; Mark B. Garred (57) ABSTRACT

A portable oxygen concentrator is disclosed. An output of a high pressure compressor is fluidly coupled to an adsorbent device that increases the concentration of oxygen gas for storage in a high pressure accumulator. The adsorbent device is purged of the collected nitrogen via a valve fluidly coupled to the outlet of the high pressure compressor and the inlet of the adsorbent device. The outlet of the adsorbent device is fluidly coupled to the high pressure accumulator through a first valve. Additionally, a re-circulation loop fluidly couples the outlet of the adsorbent device to a valved inlet of the high pressure compressor.

15 Claims, 4 Drawing Sheets

(56) References Cited

U.S. PATENT DOCUMENTS

| | | | |
|---|---|---|---|
| 2010/0300444 A1* | 12/2010 | Decker | A61M 16/024 128/204.23 |
| 2012/0304867 A1 | 12/2012 | Watanabe et al. | |
| 2013/0008438 A1 | 1/2013 | Sugawara et al. | |
| 2013/0213227 A1* | 8/2013 | Hilbig | B01D 53/22 95/54 |
| 2013/0213234 A1 | 8/2013 | Thompson et al. | |

* cited by examiner

OXYGEN CONCENTRATOR FOR HIGH PRESSURE OXYGEN DELIVERY WITH OXYGEN CIRCULATION LOOP AND IMPROVED PORTABILITY

CROSS-REFERENCE TO RELATED APPLICATIONS

The present application claims priority to U.S. Provisional Patent Application Ser. No. 61/928,110 entitled OXYGEN CONCENTRATOR FOR HIGH PRESSURE OXYGEN DELIVERY WITH OXYGEN CIRCULATION LOOP AND IMPROVED PORTABILITY filed Jan. 16, 2014, the entire disclosure of which is incorporated herein by reference.

STATEMENT RE: FEDERALLY SPONSORED RESEARCH/DEVELOPMENT

Not Applicable

BACKGROUND OF THE INVENTION

1. Technical Field of the Invention

The present disclosure relates generally to oxygen concentrators. More particularly, the present disclosure relates to an improved portable apparatus for concentrating and delivering high pressure oxygen to a ventilator.

2. Description of the Related Art

A wide range of clinical conditions may require some form of ventilation therapy. These conditions may include hypoxemia, various forms of respiratory insufficiency, and airway disorders. There are also non-respiratory and non-airway diseases that require ventilation therapy, such as congestive heart failure and neuromuscular diseases.

To improve the quality of life of many patients who require long-term ventilation therapy, ventilation systems have been developed which are miniaturized and portable. Some of these systems, for example, the NIOV system by Breathe Technologies, Inc., are so lightweight and compact that they are wearable by the patient. However, these systems also require a source of pressurized ventilation gas to operate, which is usually oxygen. One option for patients is the use of pressurized oxygen cylinders.

Improvements in battery technology have made it feasible for patients to use portable oxygen concentrators instead of pressurized oxygen cylinders with portable ventilators. Portable oxygen concentrators typically operate by pressure swing adsorption, in which ambient air is pressurized by a compressor and passed through an adsorbent sieve bed. The sieve bed is typically formed of zeolite, which preferentially adsorbs nitrogen when at high pressure while oxygen passes through. Once the sieve bed reaches its capacity to adsorb nitrogen, the pressure can be reduced. This reduction in pressure causes the adsorbed nitrogen to be desorbed so it can be purged, leaving a regenerated sieve bed that is again ready to adsorb nitrogen. With repeated cycles of this operation, an enriched oxygen gas may be generated. Typically, portable oxygen concentrators have at least two sieve beds so that at one may operate while the other is being purged of the nitrogen and vented.

Portable oxygen concentrators have a cost and convenience advantage over pressurized oxygen cylinders, due to the pressurized oxygen cylinders requiring ongoing refilling or replacement. Additionally, portable oxygen concentrators are considered to be significantly safer than pressurized oxygen cylinders. This safety consideration can have a substantial impact on a patient's quality of life as well, because many portable oxygen concentrators have been approved by the FAA for use by travelers on commercial airlines during flight, whereas personal filled oxygen cylinders are universally banned. Consequently, patients with pressurized oxygen cylinders must make expensive and time-consuming preparations with an airline ahead of time, or forego airline travel entirely.

However, despite their shortcomings, pressurized oxygen cylinders have certain advantages over portable oxygen concentrators, particularly as they relate to performance. In particular, while the pressure and rate of oxygen flow from pressurized oxygen cylinders can be adjusted to meet virtually any pressure and flow rate a patient's ventilator may requires, either continuously or periodically, conventional portable oxygen concentrations are limited in this regard, and typically do not produce enriched oxygen gas at the pressures required for some ventilator systems. Additionally, while conventional portable oxygen concentrators are capable of producing an enriched oxygen gas with a purity of around 87-96% oxygen, oxygen cylinders can output substantially pure oxygen.

In view of the foregoing, there is a need in the art for an improved portable oxygen concentrator.

BRIEF SUMMARY OF THE INVENTION

An improved portable oxygen concentrator is contemplated in which a high pressure compressor and high pressure accumulator are utilized, resulting in a potential sustained output of enriched oxygen gas at substantially higher pressures and flow rates than conventional portable oxygen concentrators. The improved portable oxygen concentrator may also include an oxygen circulation loop to allow for output of enriched oxygen gas at higher purities than conventional portable oxygen concentrators. Further, it is contemplated that even with the addition of a high pressure accumulator, the use of a compressor which may operate at substantially higher pressures and flow rates, and the attendant modifications necessary to accommodate operation at the substantially higher pressures and flow rates, the form, weight, and dimensions of the improved portable oxygen concentration may remain the same or not be excessively increased over those found in conventional portable oxygen concentrators.

In greater detail, the portable apparatus of the present invention for concentrating and delivering high pressure oxygen to a ventilator comprises an enclosure defining an air inlet, an air outlet and a flow pathway extending between the air inlet and the oxygen outlet. A high pressure compressor is disposed within the enclosure and integrated into the flow pathway, the high pressure compressor having a compressor inlet fluidly coupled to the air inlet, and a compressor outlet. An adsorbent sieve bed is also disposed within the enclosure and integrated into the flow pathway, the sieve bed having a sieve bed inlet fluidly coupled to the compressor outlet of the high pressure compressor, and a sieve bed outlet, with the sieve bed being operative to remove nitrogen from air flowing therethrough. A high pressure accumulator is also disposed within the enclosure and integrated into the flow pathway, the high pressure accumulator having an accumulator inlet fluidly coupled to the sieve bed outlet of the adsorbent sieve bed, and an accumulator outlet fluidly coupled to air outlet.

In addition, a first valve is disposed within the enclosure and integrated into the flow pathway so as to be interposed between and fluidly coupled to both the sieve bed outlet of the sieve bed and the accumulator inlet of the accumulator, the first valve being operative to prevent flow from the high pressure accumulator to the sieve bed. A second valve is also disposed within the enclosure and integrated into the flow pathway so as to be interposed between and fluidly coupled to both the accumulator outlet of the accumulator and the air outlet, the second valve being operative to meter the delivery of a concentrated oxygen gas from the high pressure accumulator to the air outlet in accordance with prescribed operational parameters of the apparatus, and to prevent flow from an exhaled breathing gas from the air outlet into the high pressure accumulator. Further, a third valve is disposed within the enclosure and integrated into the flow pathway so as to be interposed between and fluidly coupled to both the air inlet and the compressor inlet of the high pressure compressor.

As indicated above, the apparatus may also include an oxygen circulation loop. The oxygen circulation loop has a first end fluidly coupled the flow pathway between the third valve and the compressor inlet of the high pressure compressor, and a second end fluidly coupled the flow pathway between the sieve bed outlet of the sieve bed and the first valve. The oxygen circulation loop being operative to permit oxygen enriched gas to be circulated through the sieve bed, with the third valve being operative to prevent flow of the oxygen enriched gas to ambient via the air inlet.

In the apparatus of the present invention, the high pressure compressor, the sieve bed and the high pressure accumulator are sized and configured to allow the apparatus to operate at a pressure level in the range of from about 40-80 psi. The high pressure compressor, the sieve bed and the high pressure accumulator are further sized and configured to allow the apparatus to operate at a flow rate of up to at least about 10 lpm, and to further allow the apparatus to operate in a manner wherein oxygen at a concentration of up to 100% is discharged from the oxygen outlet.

The apparatus further comprises an inlet filter disposed within the enclosure and integrated into the flow pathway so as to be interposed between and fluidly coupled to both the air inlet and the compressor inlet upstream of the third valve such that air drawn into the air inlet by the high pressure compressor is passed through the inlet filter. The apparatus also further comprises an exhaust valve disposed within the enclosure and integrated into the flow pathway so as to be interposed between and fluidly coupled to both the compressor outlet of the high pressure compressor and the sieve bed inlet of the sieve bed, the exhaust valve further being in fluid communication with ambient air, and operative to exhaust nitrogen enriched gas produced by the sieve bed. Still further, the apparatus comprises a DC motor disposed within the enclosure and electrically connected to the high pressure compressor, and a DC power source disposed within the enclosure and electrically connected to the DC motor. The apparatus is configured to have a size and shape profile as allows it to be integrated into a backpack, or into a wheeled cart.

BRIEF DESCRIPTION OF THE DRAWINGS

These, as well as other features of the present invention, will become more apparent upon reference to the drawings wherein.

Common reference numerals are used throughout the drawings and detailed description to indicate like elements.

DETAILED DESCRIPTION OF THE INVENTION

The detailed description set forth below in connection with the appended drawings is intended as a description of the presently preferred embodiment of the disclosure, and is not intended to represent the only form that may be developed or utilized. The description sets forth the functions of the portable oxygen concentrator in connection with the illustrated embodiments. It is to be understood, however, that the same or equivalent functions may be accomplished by different embodiments that are also intended to be encompassed within the scope of the invention. It is further understood that the use of relational terms such as first and second and the like are used solely to distinguish one from another entity without necessarily requiring or implying any actual such relationship or order between such entities.

Figure 1:
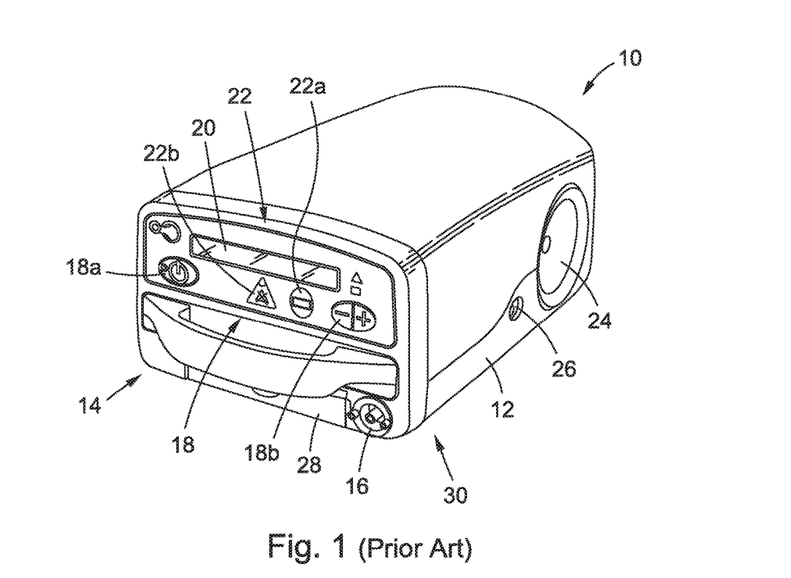
FIG. 1 is a perspective view of a prior art oxygen concentrator.

An exemplary, conventional portable oxygen concentrator or apparatus 10 is shown in FIG. 1, and is generally comprised of an enclosure 12 with a front face 14 from which various functional features of the oxygen concentrator 10 may be accessed. These include an oxygen outlet port 16 that fluidly couples the oxygen concentrator 10 to a patient ventilation interface (not shown), which in turn is connected to an airway of the patient. Furthermore, there are a series of buttons 18, including a power button 18a and previous/next buttons 18b. Using these buttons 18, various operational parameters can be modified, and the user can generally interact with a display screen 20. Additional indicators 22, such as a battery level indicator 22a, and an alarm indicator 22b, may also be included on the front face 14. These indicators may output different colored light (such as yellow and red) to signify the severity of the operational status indicated. Distal to the front face 14 is an exhaust port 24, the details of its functionality being described in further detail below. Further, disposed on the underside of the enclosure 12 not in plain view in FIG. 1 is an air intake or inlet port 30.

As the portable oxygen concentrator 10 is electrically operated, there is a power supply port 26 to which an AC-DC adapter plug (not shown) may be coupled. The adapter plug is understood to be connectable to a standard 120-240 VAC wall outlet. Additionally, the portable oxygen concentrator 10 may include a battery 28 that also supplies power for operation and may be recharged through the power supply port 26.

Figure 2:
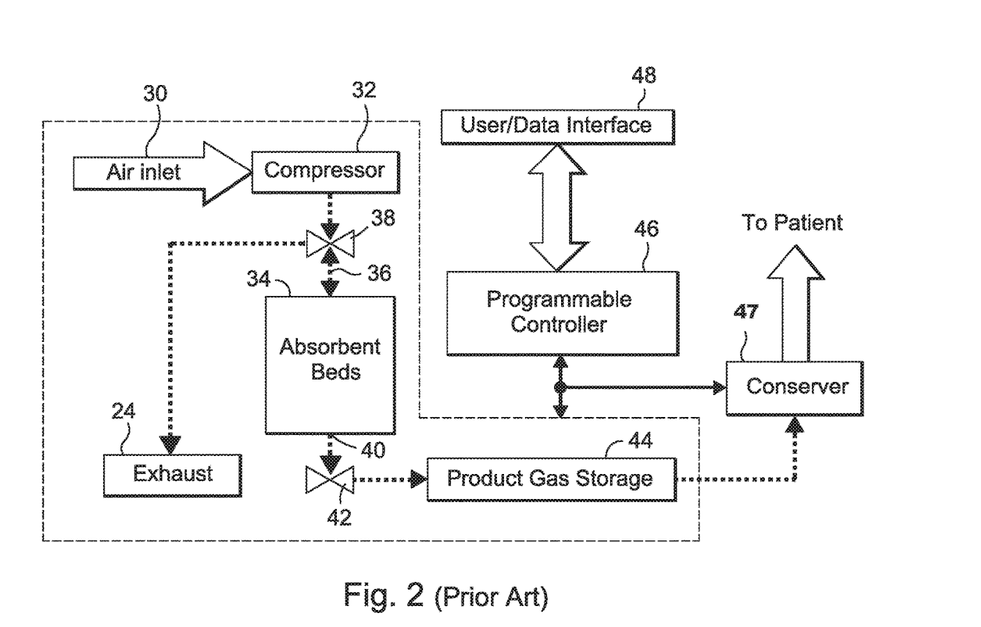
FIG. 2 is a general schematic diagram of the prior art portable oxygen concentrator shown in FIG. 1.

With reference to the block diagram of FIG. 2, the basic architecture of the oxygen concentrator 10 will be considered. Ambient air enters through the air inlet port 30. There is a compressor 32 that raises the pressure of the ambient air entering through the air inlet port 30. This compressed ambient air is then passed through adsorbent sieve beds 34 where nitrogen is scrubbed out. The adsorbent sieve beds 34 are disposed within a single unit that has a first port 36 that is fluidly coupled to the output of the compressor 32 through a first valve 38. Additionally, the unit also has a second port 40 that is connected to a second valve 42. The compressed, nitrogen-scrubbed and oxygen-rich air is output through the second port 40 through the second valve 42, and stored in a gas storage container 44, which can include additional nitrogen-adsorbent material to further increase the concentration of oxygen stored therein. The stored gas can then be delivered to the patient, typically through a conserver 47.

As will be recognized by those having ordinary skill in the art, part of the operational cycle of the adsorbent sieve beds 34 is to exhaust the nitrogen after saturation. Thus, the first valve 38 is fluidly connected to the exhaust port 24, so that this purging step can occur. In this regard, the first valve 38 is positioned to open to the exhaust port 24 during the purging operational cycle. So as to prevent the nitrogen-filled gas from entering the gas storage container 44, the second valve 42 may be closed.

The electrical signals to control the valve drivers in this manner, as well as to selectively deliver oxygen to the patient via the conserver 47, are generated from a programmable controller 46. This is understood to be a data processing device that can be pre-programmed with executable instructions. The programmable controller 46 generates signals in response to such instructions, and the results of the instructions may be shown on the display screen 20. The execution sequence of the instructions may be modified based on inputs received from the buttons 18. The combination of the buttons 18 and the display screen 20, along with data and executable instructions related thereto, may be generally referred to as a user interface 48. The instructions and other related data may be stored on an on-board memory device.

Figure 3:
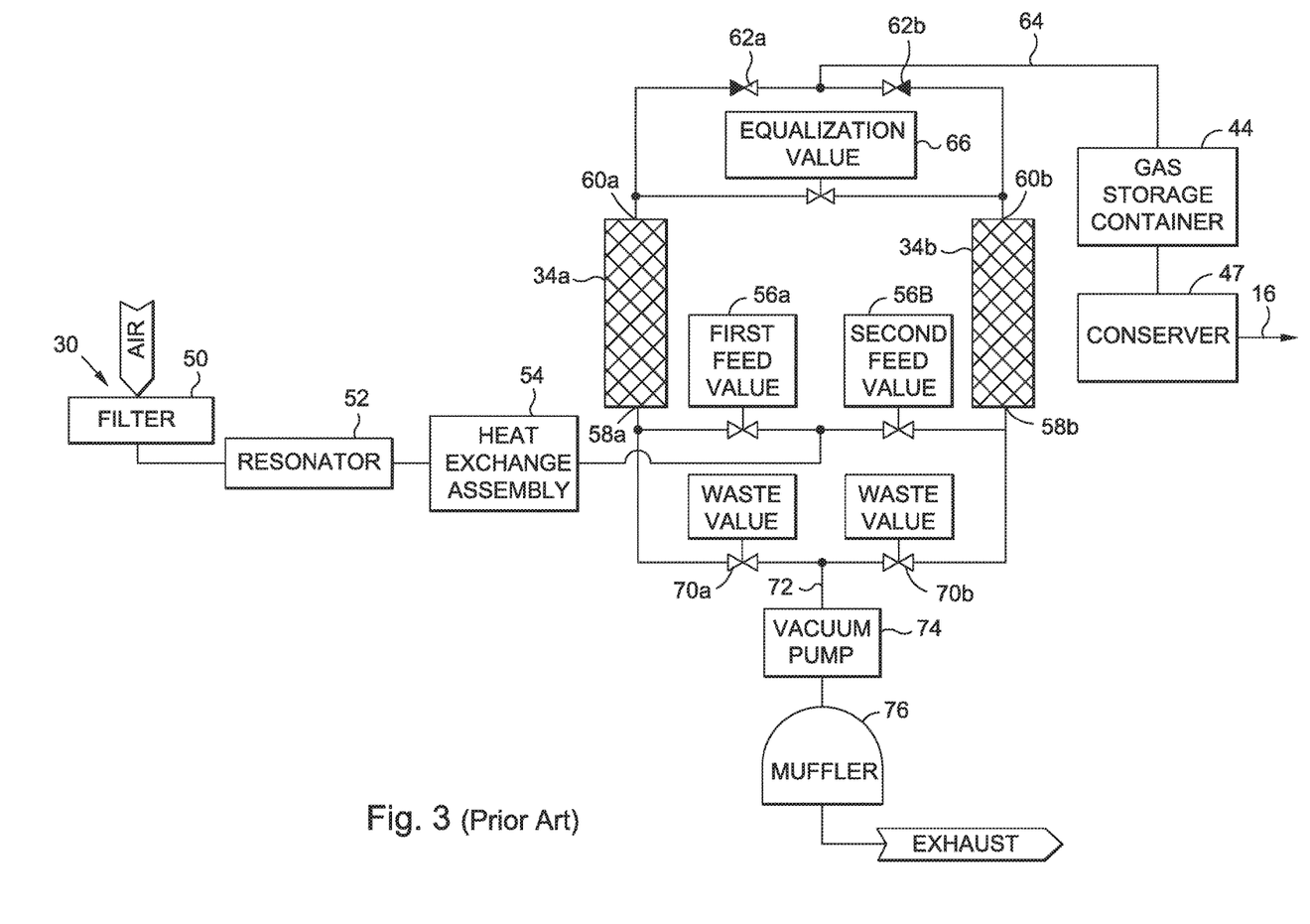
FIG. 3 is a more detailed schematic diagram of the prior art portable oxygen concentrator shown in FIG. 1.

As shown in FIG. 3, a more detailed schematic of a conventional portable oxygen concentrator 10, the sieve beds 34 may comprise at least two adsorbent sieve beds 34a, 34b so that one may be operating while the other is being purged. Again, the ambient air is supplied through the air inlet port 30, the intake gas flow pathway of which may be connected to a filter 50 as well as a resonator 52 that suppresses noise. The ambient air may then pass through a heat exchanger assembly 54, and alternatively passed to either the first adsorbent sieve bed 34a or the second adsorbent sieve bed 34b through first and second feed valves 56a, 56b, respectively. The first adsorbent sieve bed 34a includes an inlet 58a and an outlet 60a, while the second adsorbent sieve bed 34b includes a corresponding inlet 58b and an outlet 60b. The adsorbent sieve beds 34a, 34b fractionate the air stream into the desired concentration of oxygen gas. The adsorbent material used for the adsorbent sieve beds 34a, 34b to separate nitrogen from the ambient air may be a synthetic zeolite or other known adsorber material having equivalent properties.

The usable portion of the oxygen enriched gas passing through the adsorbent sieve beds 34a, 34b is directed out through the respective outlets 60a, 60b, and then to check valves 62a, 62b, respectively, with the two separate gas flow pathways being combined at a manifold 64. As indicated above, the produced oxygen-enriched gas may then be stored in the gas storage container 44 and otherwise delivered to the patient via the conserver 47. The unneeded, nitrogen-enriched gas that is also generated by the adsorbent sieve beds 34a, 34b are alternately exhausted by activating a properly timed equalization valve 66, along with waste valves 70a, 70b that are coupled to the inlets 58a, 58b of the first and second adsorbent sieve bed 34a, 34b, respectively. The two outputs of the waste valves 70a, 70b are combined in another manifold 72, which in turn is fluidly coupled to a vacuum pump 74 that draws the waste nitrogen alternately from each of the adsorbent sieve beds 34a, 34b. The outlet of the vacuum pump 74 may also be coupled to a muffler 76 for reduction of noise.

Existing portable oxygen concentrators typically output enriched oxygen gas at flow rates between 0.5-10 LPM and at pressures between 1-10 PSI. It is contemplated, however, that an improved portable oxygen concentrator may output enriched oxygen gas at pressures previously achievable in a portable setting only with compressed oxygen tanks. It is contemplated that in accordance with the present invention, a high pressure compressor may be used so as to substantially increase output pressures of enriched oxygen gas. More particularly, pressure levels of between 40-80 PSI may be achieved, while also achieving a high flow rate of 10 LPM and an oxygen discharge at the from the oxygen outlet at a concentration of up to 100%.

Figure 4:
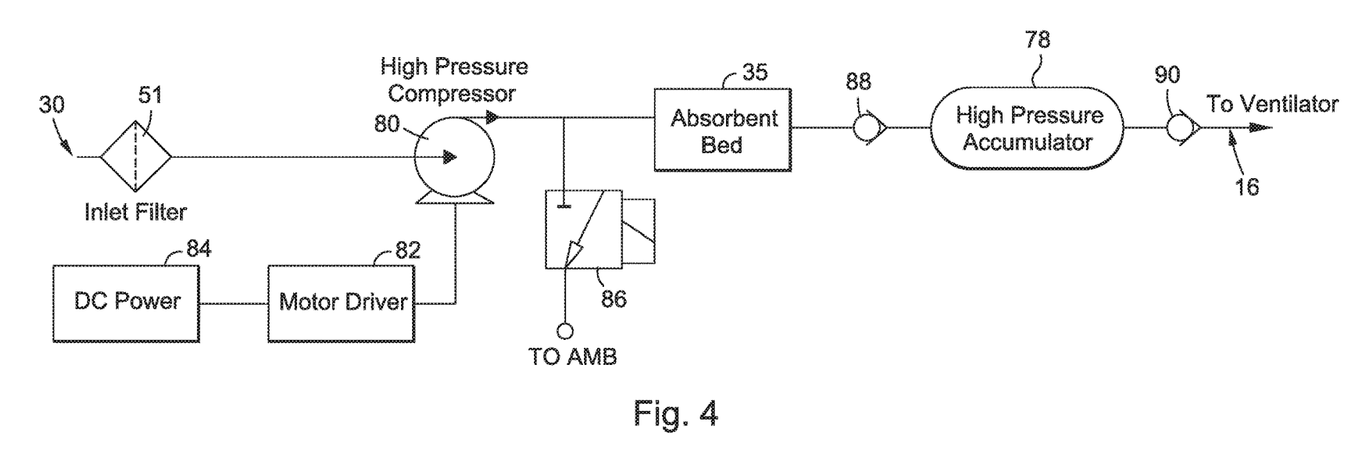
FIG. 4 is a block diagram of a first embodiment of the improved portable oxygen concentrator of the present invention as includes a high pressure compressor and a high pressure accumulator.

The block diagram of FIG. 4 shows one such embodiment. It is contemplated that the various components shown and labeled in FIG. 4, and as described in more detail below, may be integrated into the enclosure 12 of the apparatus 10 in substitution for those features shown and described above in relation to FIGS. 2 and 3. In this regard, an improved oxygen concentrator or apparatus 10a is envisioned which comprises the combination of those features shown and described in FIG. 1 as combined with those corresponding to FIG. 4. Thus, in the description below, those features of the apparatus 10 common to the apparatus 10a will be described in terms of their relationship to the features shown in FIG. 4.

In the apparatus 10a, there is a high pressure accumulator 78, along with a high pressure compressor 80 that is driven by a direct current (DC) motor 82. The high pressure compressor 80 draws in ambient air through the air inlet port 30 and an inlet filter 51. The DC motor 82 is powered by a DC source 84, which may be the battery 28. However, there may be additional circuitry that conditions the power signal from the battery 28 to a level that can drive the DC motor 82, and so the DC source 84 is understood to encompass such circuitry. The high pressure compressor 80 drives the filtered ambient air to an adsorbent sieve bed 35, which is understood to remove nitrogen and thereby increase the concentration of oxygen.

The output of the adsorbent sieve bed 35 is connected to a valve 88 and then to a high pressure accumulator 78, where it may be stored if not immediately needed, possibly in substantial quantities. Its pressure and/or flow rate may be maintained or increased prior to delivery to the patient. Such a configuration may allow the use of the improved portable oxygen concentrator with ventilators which may take advantage of or require these higher oxygen flow rates or pressures. There may be an additional valve 90 that meters the delivery of the concentrated oxygen gas in accordance with desired operational parameters. The valve 88 may be one-way so that the concentrated oxygen gas stored in the high pressure accumulator 78 does not flow in a reverse direction back to the adsorbent sieve bed 35. Similarly, the valve 90 may also be one-way to prevent exhaled breathing gas from the ventilator to flow into the high pressure accumulator 78 via the oxygen outlet port 16.

The operation of the adsorbent sieve bed 35 is similar to that of the sieve beds 34a, 34b described above, but in accordance with one embodiment of the present disclosure, it may be possible to utilize a single adsorbent element for adsorbing nitrogen rather than the aforementioned two, without the synchronized feed and waste valves 56, 70 as is typical in conventional portable oxygen concentrators. The portable oxygen concentrator or apparatus 10a may incorporate a single exhaust valve 86 having an outlet to ambient or to the exhaust port 24, with the nitrogen-enriched gasses produced from the operation of the adsorbent sieve bed 35 being exhausted therewith. In typical portable oxygen concentrators, having two sieve beds allows enriched oxygen gas to still be output while one bed is being purged of nitrogen. The use of a high pressure accumulator 78, however, will still allow enriched oxygen gas to flow to the patient from while the sieve bed 35 is being purged, without requiring coordination between multiple sieve beds. Therefore, an improved portable oxygen concentrator (i.e., the apparatus 10a) may be constructed with only one sieve bed 35, rather than two or more. In the apparatus 10a, the potential increased spatial footprint of the high pressure blower or compressor 80 and/or the high pressure concentrator or accumulator 78 may be partially or even completely offset by the efficiency gain in requiring only the single sieve bed 35, as well as other efficiency gains. It is thus contemplated that the apparatus 10a may have a footprint similar to that, or even unchanged from, a conventional portable oxygen concentrator such as the portable oxygen concentrator 10, notwithstanding the higher density materials in the various conduits, and the additional sealing members that may be needed to accommodate the higher pressure levels and flow rates.

Figure 5:
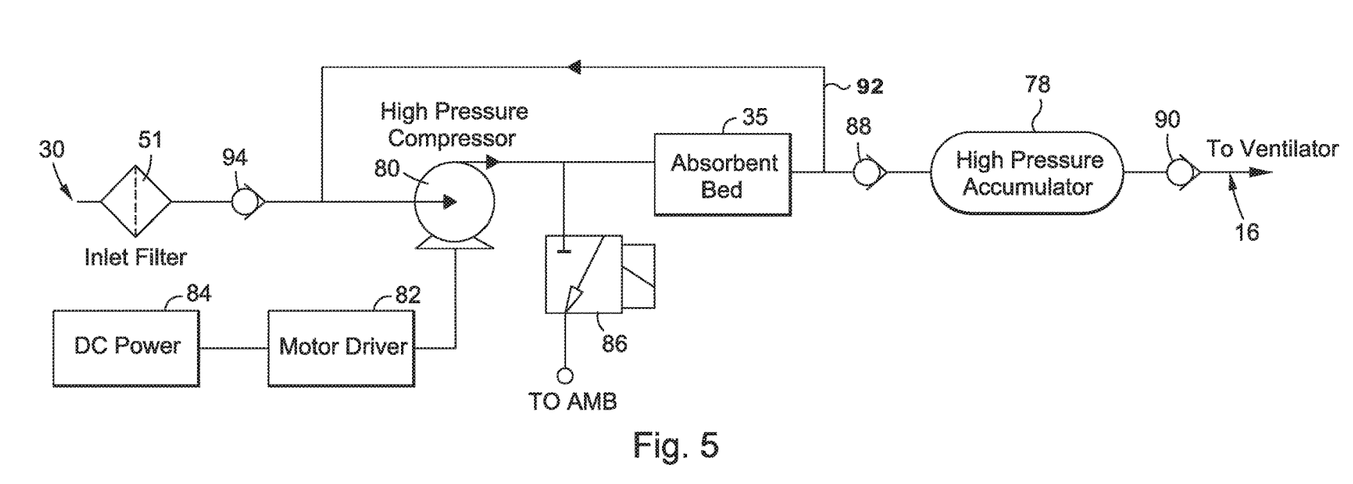
FIG. 5 is a block diagram of a second embodiment of the improved portable oxygen concentrator of the present invention as includes a high pressure compressor, a high pressure accumulator, and an oxygen circulation loop.

An additional contemplated embodiment is shown schematically in FIG. 5. It is also contemplated that the various components shown and labeled in FIG. 5, and as described in more detail below, may be integrated into the enclosure 12 of the apparatus 10 in substitution for those features shown and described above in relation to FIGS. 2 and 3. In this regard, an improved oxygen concentrator or apparatus 10b is envisioned which comprises the combination of those features shown and described in FIG. 1 as combined with those corresponding to FIG. 5. Thus, in the description below, those features of the apparatus 10 common to the apparatus 10b will be described in terms of their relationship to the features shown in FIG. 5.

The primary distinction between the apparatus 10a and the apparatus 10b lies in the inclusion of an oxygen circulation loop 92 in the apparatus 10b to permit enriched oxygen gas to be circulated through the adsorbent sieve bed 35 one or more times, resulting in the production of an enriched oxygen gas of a substantially higher purity. It is expressly contemplated that this additional embodiment includes the high pressure compressor 80 that is driven by the DC motor driver 82, which in turn is powered by the DC source 84. Furthermore, there is the high pressure accumulator 78 that stores the oxygen-enriched gas that is generated from the adsorbent sieve bed 35. The valve 90 is understood to regulate the output flow from the high pressure accumulator 78, and the valve 86 is understood to be used for exhausting the nitrogen-enriched gas that is generated as a by-product by the adsorbent sieve bed 35.

As indicated above, the valve 88 regulates the one-way directional flow of the concentrated oxygen gas into the high pressure accumulator 78, and ensures that there is no reverse flow back to the adsorbent sieve bed 35. The oxygen circulation loop 92 is tapped upstream of the valve 88, and is recirculated into the ambient air inlet of the high pressure compressor 80. In order to prevent the re-circulated, oxygen-enriched gas from the adsorbent sieve bed 35 to flow back to ambient, there is another one-way valve 94 at the inlet of the high pressure compressor 80. As such, enriched oxygen gas emerging from the adsorbent sieve bed 35 may enter the oxygen circulation loop 92 and be recirculated through the high pressure compressor 80 and the sieve bed 35, either alone or after mixing with additional ambient air, resulting in the production of enriched oxygen gas having higher purity.

Figure 6:
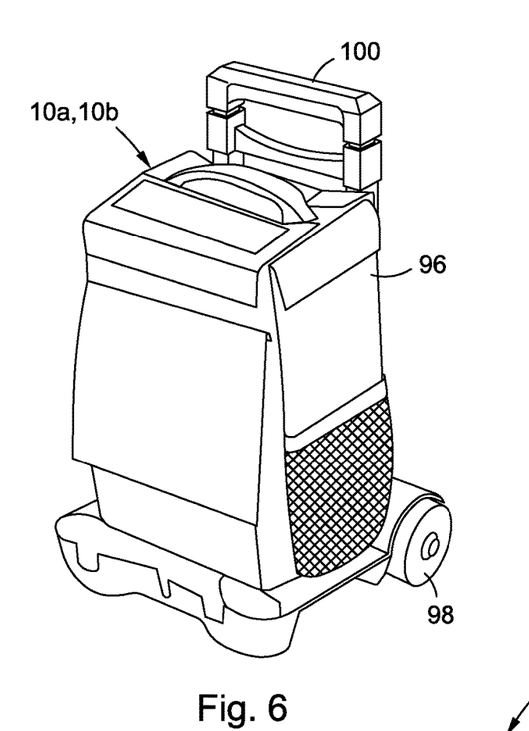
FIG. 6 is a perspective view of the portable oxygen concentrator of the present invention in a wheeled cart configuration.
Figure 7:
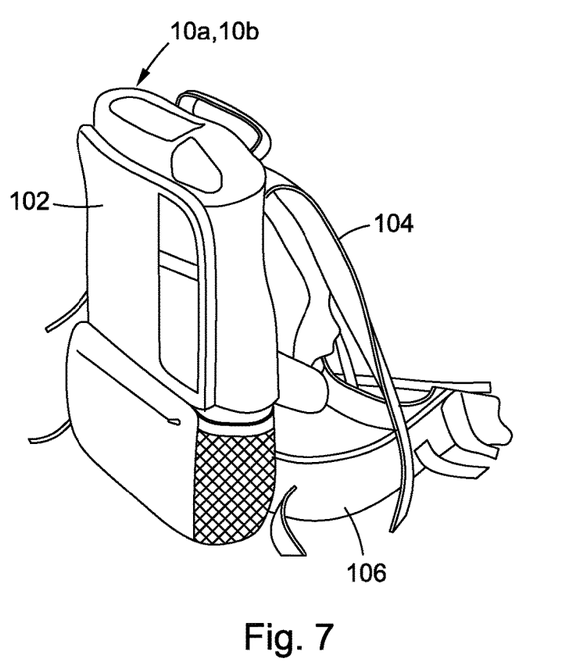
FIG. 7 is a perspective view of the portable oxygen concentrator of the present invention in a backpack configuration.

As shown in FIGS. 6 and 7, the portable oxygen concentrators or apparatuses 10a, 10b may be constructed to be transported or worn by a patient, such as in a wheeled cart or a backpack configuration. FIG. 6 in particular shows a wheeled cart configuration in which the enclosure 12 of either of the apparatuses 10a, 10b is placed in a conforming cart 96 with a set of wheels 98. The cart 96 may also include a handle 100 that can be used to tilt the cart 96 (and the portable oxygen concentrator 10a or 10b) about the rotational axis of the wheels 98, and pushed/pulled. The backpack configuration shown in FIG. 7 similarly includes a pouch portion 102 that is shaped in accordance with the enclosure 12 of either of the apparatuses 10a, 10b. Also attached to the pouch portion is a pair of shoulder straps 104 that can be positioned on the torso of the patient. Additional lumbar support may be provided via transverse kidney straps 106. Those having ordinary skill in the art will readily recognize other possible forms in which the portable oxygen concentrator 10a, 10b may be carried, including various configurations of bags and the like.

It is contemplated that the apparatuses 10a, 10b may each further be outfitted with the programmable controller 46 to serve as part of a user interface 48 and shown and described above in relation to FIGS. 1 and 2 in the context of the apparatus 10. Such programmable controller 46, and hence the user interface 48, would be in operative communication with, for example, compressor 80, the exhaust valve 86, the motor driver 82, and the DC power source 84.

The spatial footprint of a portable oxygen concentrator is an important consideration in the construction of the improved portable oxygen concentrator 10a, 10b. The use of the high pressure accumulator 78, along with the changes to the architecture to accommodate the higher pressures and flow rates as well as the inclusion of an oxygen circulation loop 92 in one embodiment, may affect the size, weight, and other physical dimensions of the portable oxygen concentrator 10a, 10b. Although the reduction of the overall footprint is more highly prioritized in a device intended to be portable, a slight increase therewith may be offset due to the advantages to be found in certain embodiments as discussed above, including a reduction in the number of components such as valves and adsorbent beds, and the attendant reductions in operating complexity, size, cost, maintenance, and so forth. Thus, apparatuses 10a, 10b, while providing superior performance over traditional oxygen concentrators by supplying enriched oxygen gas at comparatively, substantially higher oxygen concentrations, volumes, pressures and flow rates, do so with a size penalty.

This disclosure provides exemplary embodiments of the improved portable oxygen concentrator or apparatus 10a, 10b. The scope of the present invention is not limited by these exemplary embodiments. Numerous variations, whether explicitly provided for by the specification or implied by the specification, such as variations in structure, dimension, type of material and manufacturing process may be implemented by one of skill in the art in view of this disclosure. For example, it is contemplated that those features depicted in FIGS. 4 and 5 and describe above may be integrated into an apparatus having structural and functional features differing from those of the apparatus 10, such apparatus 10 comprising only one exemplary environment suitable for the integration of the variants shown and described in relation to FIGS. 4 and 5.

What is claimed is:

1. A portable apparatus for concentrating and delivering high pressure oxygen to a ventilator, the apparatus comprising:
    an enclosure defining an air inlet, an oxygen outlet and a flow pathway extending between the air inlet and the oxygen outlet;
    a high pressure compressor disposed within the enclosure and integrated into the flow pathway, the high pressure compressor having a compressor inlet fluidly coupled to the air inlet, and a compressor outlet;
    an adsorbent sieve bed disposed within the enclosure and integrated into the flow pathway, the sieve bed having a sieve bed inlet fluidly coupled to the compressor outlet of the high pressure compressor, and a sieve bed outlet, with the sieve bed being operative to remove nitrogen from air flowing therethrough;
    a high pressure accumulator disposed within the enclosure and integrated into the flow pathway, the high pressure accumulator having an accumulator inlet fluidly coupled to the sieve bed outlet of the adsorbent sieve bed, and an accumulator outlet fluidly coupled to the oxygen outlet;
    a first valve disposed within the enclosure and integrated into the flow pathway so as to be interposed between and fluidly coupled to both the sieve bed outlet of the sieve bed and the accumulator inlet of the accumulator, the first valve being operative to prevent flow from the high pressure accumulator to the sieve bed;
    a third valve disposed within the enclosure and integrated into the flow pathway so as to be interposed between and fluidly coupled to both the air inlet and the compressor inlet of the high pressure compressor; and
    an oxygen circulation loop having a first end fluidly coupled to the flow pathway between the third valve and the compressor inlet of the high pressure compressor, and a second end fluidly coupled to the flow pathway between the sieve bed outlet of the sieve bed and the first valve;
    the oxygen circulation loop being operative to permit oxygen enriched gas to be circulated through the sieve bed, with the third valve being operative to prevent flow of the oxygen enriched gas to ambient via the air inlet;
    the high pressure compressor, the sieve bed and the high pressure accumulator being sized and configured to allow the apparatus to operate at a pressure level in the range of from about 40-80 psi.

2. The apparatus of claim 1 wherein the high pressure compressor, the sieve bed and the high pressure accumulator are further sized and configured to allow the apparatus to operate in a manner wherein oxygen at a concentration of up to 100% is discharged from the oxygen outlet.

3. The apparatus of claim 1 further comprising an inlet filter disposed within the enclosure and integrated into the flow pathway so as to be interposed between and fluidly coupled to both the air inlet and the compressor inlet such that air drawn into the air inlet by the high pressure compressor is passed through the inlet filter.

4. The apparatus of claim 1 further comprising a second valve disposed within the enclosure and integrated into the flow pathway so as to be interposed between and fluidly coupled to both the accumulator outlet of the accumulator and the air outlet, the second valve being operative to meter the delivery of a concentrated oxygen gas from the high pressure accumulator to the air outlet in accordance with prescribed operational parameters of the apparatus, and to prevent flow of an exhaled breathing gas from the air outlet into the high pressure accumulator.

5. The apparatus of claim 1 further comprising an exhaust valve disposed within the enclosure and integrated into the flow pathway so as to be interposed between and fluidly coupled to both the compressor outlet of the high pressure compressor and the sieve bed inlet of the sieve bed, the exhaust valve further being in fluid communication with ambient air, and operative to exhaust nitrogen enriched gas produced by the sieve bed.

6. The apparatus of claim 1 further comprising:
    a DC motor disposed within the enclosure and electrically connected to the high pressure compressor; and
    a DC power source disposed within the enclosure and electrically connected to the DC motor.

7. The apparatus of claim 1 wherein the apparatus is configured to have a size and shape profile as allows it to be integrated into a backpack.

8. A portable apparatus for concentrating and delivering high pressure oxygen to a ventilator, the apparatus comprising:
    an enclosure defining an air inlet, an air outlet and a flow pathway extending between the air inlet and the oxygen outlet;
    a high pressure compressor disposed within the enclosure and integrated into the flow pathway, the high pressure compressor having a compressor inlet fluidly coupled to the air inlet, and a compressor outlet;
    an adsorbent sieve bed disposed within the enclosure and integrated into the flow pathway, the sieve bed having a sieve bed inlet fluidly coupled to the compressor outlet of the high pressure compressor, and a sieve bed outlet, with the sieve bed being operative to remove nitrogen from air flowing therethrough;
    a high pressure accumulator disposed within the enclosure and integrated into the flow pathway, the high pressure accumulator having an accumulator inlet fluidly coupled to the sieve bed outlet of the adsorbent sieve bed, and an accumulator outlet fluidly coupled to air outlet;
    a first valve disposed within the enclosure and integrated into the flow pathway so as to be interposed between and fluidly coupled to both the sieve bed outlet of the sieve bed and the accumulator inlet of the accumulator, the first valve being operative to prevent flow from the high pressure accumulator to the sieve bed;
    a second valve disposed within the enclosure and integrated into the flow pathway so as to be interposed between and fluidly coupled to both the accumulator outlet of the accumulator and the air outlet, the second valve being operative to meter the delivery of a concentrated oxygen gas from the high pressure accumulator to the air outlet in accordance with prescribed operational parameters of the apparatus, and to prevent flow from an exhaled breathing gas from the air outlet into the high pressure accumulator;
    a third valve disposed within the enclosure and integrated into the flow pathway so as to be interposed between and fluidly coupled to both the air inlet and the compressor inlet of the high pressure compressor; and an oxygen circulation loop having a first end fluidly coupled to the flow pathway between the third valve and the compressor inlet of the high pressure compressor, and a second end fluidly coupled to the flow pathway between the sieve bed outlet of the sieve bed and the first valve;

the oxygen circulation loop being operative to permit oxygen enriched gas to be circulated through the sieve bed, with the third valve being operative to prevent flow of the oxygen enriched gas to ambient via the air inlet.

9. The apparatus of claim 8 wherein the high pressure compressor, the sieve bed and the high pressure accumulator are sized and configured to allow the apparatus to operate at a pressure level in the range of from about 40-80 psi.

10. The apparatus of claim 9 wherein the high pressure compressor, the sieve bed and the high pressure accumulator are further sized and configured to allow the apparatus to operate at a flow rate of up to at least about 10 lpm.

11. The apparatus of claim 10 wherein the high pressure compressor, the sieve bed and the high pressure accumulator are further sized and configured to allow the apparatus to operate in a manner wherein oxygen at a concentration of up to 100% is discharged from the oxygen outlet.

12. The apparatus of claim 8 further comprising an inlet filter disposed within the enclosure and integrated into the flow pathway so as to be interposed between and fluidly coupled to both the air inlet and the compressor inlet upstream of the third valve such that air drawn into the air inlet by the high pressure compressor is passed through the inlet filter.

13. The apparatus of claim 8 further comprising an exhaust valve disposed within the enclosure and integrated into the flow pathway so as to be interposed between and fluidly coupled to both the compressor outlet of the high pressure compressor and the sieve bed inlet of the sieve bed, the exhaust valve further being in fluid communication with ambient air, and operative to exhaust nitrogen enriched gas produced by the sieve bed.

14. The apparatus of claim 8 further comprising:
a DC motor disposed within the enclosure and electrically connected to the high pressure compressor; and
a DC power source disposed within the enclosure and electrically connected to the DC motor.

15. The apparatus of claim 14 wherein the apparatus is configured to have a size and shape profile as allows it to be integrated into a backpack.

* * * * *